United States Patent
Morard et al.

(10) Patent No.: US 9,836,833 B2
(45) Date of Patent: Dec. 5, 2017

(54) NON-INTRUSIVE MEASUREMENT OF THE VOLUME DENSITY OF A PHASE IN A PART

(71) Applicant: Safran, Paris (FR)

(72) Inventors: Vincent Morard, Melun (FR); Estelle Parra, Fontenay le Vicomte (FR); David Tourais, Paris (FR)

(73) Assignee: SAFRAN, Paris (FR)

( * ) Notice: Subject to any disclaimer, the term of this patent is extended or adjusted under 35 U.S.C. 154(b) by 0 days.

(21) Appl. No.: 15/102,663

(22) PCT Filed: Dec. 3, 2014

(86) PCT No.: PCT/FR2014/053147
§ 371 (c)(1),
(2) Date: Jun. 8, 2016

(87) PCT Pub. No.: WO2015/086956
PCT Pub. Date: Jun. 18, 2015

(65) Prior Publication Data
US 2017/0004613 A1     Jan. 5, 2017

(30) Foreign Application Priority Data
Dec. 13, 2013 (FR) .................................. 13 62554

(51) Int. Cl.
*G06K 9/00* (2006.01)
*G06T 7/00* (2017.01)
(Continued)

(52) U.S. Cl.
CPC ......... *G06T 7/0004* (2013.01); *G01N 23/046* (2013.01); *G06T 15/08* (2013.01);
(Continued)

(58) Field of Classification Search
CPC ........... G01N 23/046; G01N 2223/401; G01N 2223/419; G01N 2223/601; G06T 15/08;
(Continued)

(56) References Cited

U.S. PATENT DOCUMENTS 5,617,461 A     4/1997 Schreiner
5,960,056 A *   9/1999 Lai .......................... A61B 6/032
                                                             378/15

(Continued)

FOREIGN PATENT DOCUMENTS

WO         96/42022 A1    12/1996

OTHER PUBLICATIONS

English translation of International Search Report issued in Application No. PCT/FR2014/053147 dated Mar. 2, 2015.
(Continued)

*Primary Examiner* — Ali Bayat
(74) *Attorney, Agent, or Firm* — Pearne & Gordon LLP

(57) ABSTRACT

Method and system for non-intrusive measurement of volume density of a specific phase in a part, comprising: processor producing a volume image of the part, the image being formed by a three-dimensional grid of voxels, the values of which indicate the disposition of the specific phase in the part, processor associating a binary coefficient with each voxel of the volume image, thus constructing an initial three-dimensional matrix representation of binary coefficients representing a presence or absence of the specific phase in zones of the part corresponding to the voxels, processor convoluting the initial matrix representation with a convolution matrix kernel corresponding to a predetermined reference volume, the convolution performed by effecting a composition of three (successive) monodimensional convolutions in three independent directions, thus forming a resultant matrix representation, each resultant (Continued)

coefficient of which represents a volume ratio (the density) of the specific phase in the reference volume.

9 Claims, 4 Drawing Sheets

(51) Int. Cl.
*G01N 23/04* (2006.01)
*G06T 15/08* (2011.01)

(52) U.S. Cl.
CPC . *G01N 2223/401* (2013.01); *G01N 2223/419* (2013.01); *G01N 2223/601* (2013.01); *G06T 2200/04* (2013.01); *G06T 2207/10081* (2013.01); *G06T 2207/20021* (2013.01); *G06T 2207/30164* (2013.01)

(58) Field of Classification Search
CPC ....... G06T 2200/04; G06T 2207/10081; G06T 2207/20021; G06T 2207/0004; G06T 2207/30164
See application file for complete search history.

(56) References Cited

U.S. PATENT DOCUMENTS

| | | | |
|---|---|---|---|
| 6,075,871 A | 6/2000 | Simanovsky | |
| 6,118,841 A * | 9/2000 | Lai | A61B 6/032 378/14 |
| 6,173,029 B1 * | 1/2001 | Xie | G06T 11/005 378/4 |
| 7,486,839 B2 * | 2/2009 | Moriguchi | G01R 33/285 382/131 |
| 8,781,197 B2 * | 7/2014 | Wang | G01R 33/54 382/131 |
| 2010/0278440 A1 | 11/2010 | Dragovich et al. | |

OTHER PUBLICATIONS

Search Report issued in French Patent Application No. FR 13 62554 dated Apr. 24, 2014.

Wolthaus J., et al. "Reconstruction of a time-average midposition CT scan for radiotherapy planning of lung cancer patients using deformable registration" IN: Medical Physics, Aug. 11, 2008, vol. 35, No. 9, pp. 3998-4011.

Paik D.S., et al. "Surface normal overlap: a computer-aided detection algorithm with application to colonic polyps and lung nodules in helical CT" IN: IEEE Transaction on Medical Imaging, Jun. 1, 2004, vol. 23, No. 6, pp. 661-675.

Written Opinion issued in Application No. PCT/FR2014/053147 dated Mar. 2, 2015.

\* cited by examiner

FIG.4

NON-INTRUSIVE MEASUREMENT OF THE VOLUME DENSITY OF A PHASE IN A PART

TECHNICAL FIELD

The present invention relates in general terms to a non-destructive method for characterising materials and more particularly measuring the volume density of a distinctive phase in the material of a part.

PRIOR ART

Safety and reliability are major preoccupations in several industrial fields. By way of example, in the aeronautical field, the procedures for designing and producing the various parts of an aircraft engine have recourse to various types of analysis and inspection for guaranteeing the reliability of the engine.

Concerning the structural aspects of the materials, these inspections comprise optical imaging techniques such as tomography. The latter technique has been the subject of numerous publications and the principle thereof consists of constructing a volume image of an object from a series of images of various cross sections of the object.

The tomography technique can be used for detecting and then identifying a specific or distinctive phase in a material of the body. In particular, this technique is used for characterising or measuring, at each point on the tomographic image, the volume ratio or the density of the specific phase compared with a reference volume that is defined in advance. It should be noted that the term "phase" may designate a defect, a porosity, strands, glass fibres, etc. in the material of the body being analysed.

Currently it is possible for example to use software of the Aviso Fire® type for calculating the volume porosity ratio in a tomographic image. For all the voxels of the image, the measurement of the volume ratio is calculated by centring the reference volume on a current voxel and then running through all the voxels belonging to this reference volume in order to count the voxels indicating porosities. Once the counting has ended, the ratio between the volume occupied by the porosity and the reference volume is stored in an output image.

However, the dimensions of the tomographic image and of the reference volume may be fairly great according to requirements, making this method inappropriate for production inspections. This is because the algorithmic complexity depends on the product of the number N of voxels in the image multiplied by the number L of voxels in the reference volume. Thus the computing time depends on the size of the image and the size of the reference volume in O(NL) and may greatly exceed several hours per image.

The object of the present invention is consequently to remedy the aforementioned drawbacks by proposing a method and system for the non-intrusive measurement of the volume density of a distinctive phase in a part, which is simple to implement and makes it possible to reduce the number of operations and consequently to accelerate the computing time.

DISCLOSURE OF THE INVENTION

The present invention is defined by a method for the non-intrusive measurement of the volume density of a specific phase in a part, comprising the following steps:

producing a volume image of said part, said image being formed by a three-dimensional grid of voxels, the values of which indicate the disposition of said specific phase in said part, associating a binary coefficient with each voxel of said volume image, thus constructing an initial three-dimensional matrix representation of binary coefficients, said binary coefficients representing a presence or absence of said specific phase in zones of said part corresponding to the voxels, convoluting said initial matrix representation with a convolution matrix kernel corresponding to a predetermined reference volume, said convolution being performed by effecting a composition of three monodimensional convolutions in three independent directions, thus forming a resultant matrix representation, each resultant coefficient of which represents a volume ratio (or density) of said specific phase in said reference volume.

This method makes it possible to reduce to the maximum extent the redundancy of the calculation steps and to be free from the size of the reference volume, thus considerably reducing the processing time, which in addition is independent of the content of the image.

Advantageously, the convolution of said initial matrix representation comprises the following steps:

extracting each row of said initial matrix representation in a first direction in order to convolute it with said convolution kernel in said first direction, thus forming a first intermediate matrix representation, extracting each row of said first intermediate matrix representation in a second direction in order to convolute it with said convolution kernel in said second direction, thus forming a second intermediate matrix representation, and extracting each row of said second intermediate matrix representation in a third direction in order to convolute it with said convolution kernel in said third direction, thus forming said resultant matrix representation.

The decomposition of a 3D convolution into three 1D convolutions simplifies implementation and considerably reduces the number of computing operations.

Advantageously, the method comprises a parallelisation of the extraction and convolution operations on the various rows of each matrix representation.

The parallelisation of the processing makes it possible to best exploit the power of the processing means.

Advantageously, each current matrix representation among the intermediate and resultant representations is constructed by replacing the coefficients of the previous matrix representation with current coefficients.

This further accelerates the computing time.

According to one aspect of the present invention, the convolution kernel is an averaging kernel weighting each coefficient identically. The convolution kernel corresponds to a parallelepipedal reference volume.

Advantageously, said part is a part of an aircraft engine.

The invention also relates to a system for the non-intrusive measurement of the volume density of a specific phase in a part, comprising:

processing means for producing a volume image of said part, said image being formed by a three-dimensional grid of voxels, the values of which indicate the disposition of said specific phase in said part, processing means for associating a binary coefficient with each voxel of said volume image, thus constructing an initial three-dimensional matrix representation of binary coefficients, said binary coefficients representing a presence or absence of said specific phase in zones of said part corresponding to the voxels, processing means for convoluting said initial matrix representation with a convolution matrix kernel corresponding to a predetermined reference volume, said convolution being performed by effecting a composition of three monodimensional convolutions in three independent directions, thus forming a resultant matrix representation, each resultant coefficient of which represents a volume ratio (or density) of said specific phase in said reference volume.

Advantageously, the system comprises:

processing means for extracting each row of said initial matrix representation in a first direction in order to convolute it with said convolution kernel in said first direction, thus forming a first intermediate matrix representation, processing means for extracting each row of said first intermediate matrix representation in a second direction in order to convolute it with said convolution kernel in said second direction, thus forming a second intermediate matrix representation, and processing means for extracting each row of said second intermediate matrix representation in a third direction in order to convolute it with said convolution kernel in said third direction, thus forming said resultant matrix representation.

Advantageously, the processing means are configured to parallelise extraction and convolution operations on the various rows of each matrix representation.

BRIEF DESCRIPTION OF THE DRAWINGS

Other features and advantages of the invention will emerge from a reading of preferential embodiments of the invention done with reference to the accompanying figures, among which:

FIG. 4 is an example relating to a two-dimensional image illustrating the convolution principle according to the invention.

DETAILED DISCLOSURE OF PARTICULAR EMBODIMENTS

The principle of the invention consists of running through all the points on a volume image in order to measure thereon the volume density of a specific phase while reducing to the maximum extent the data redundancy caused during the computation of this measurement.

Figure 1:
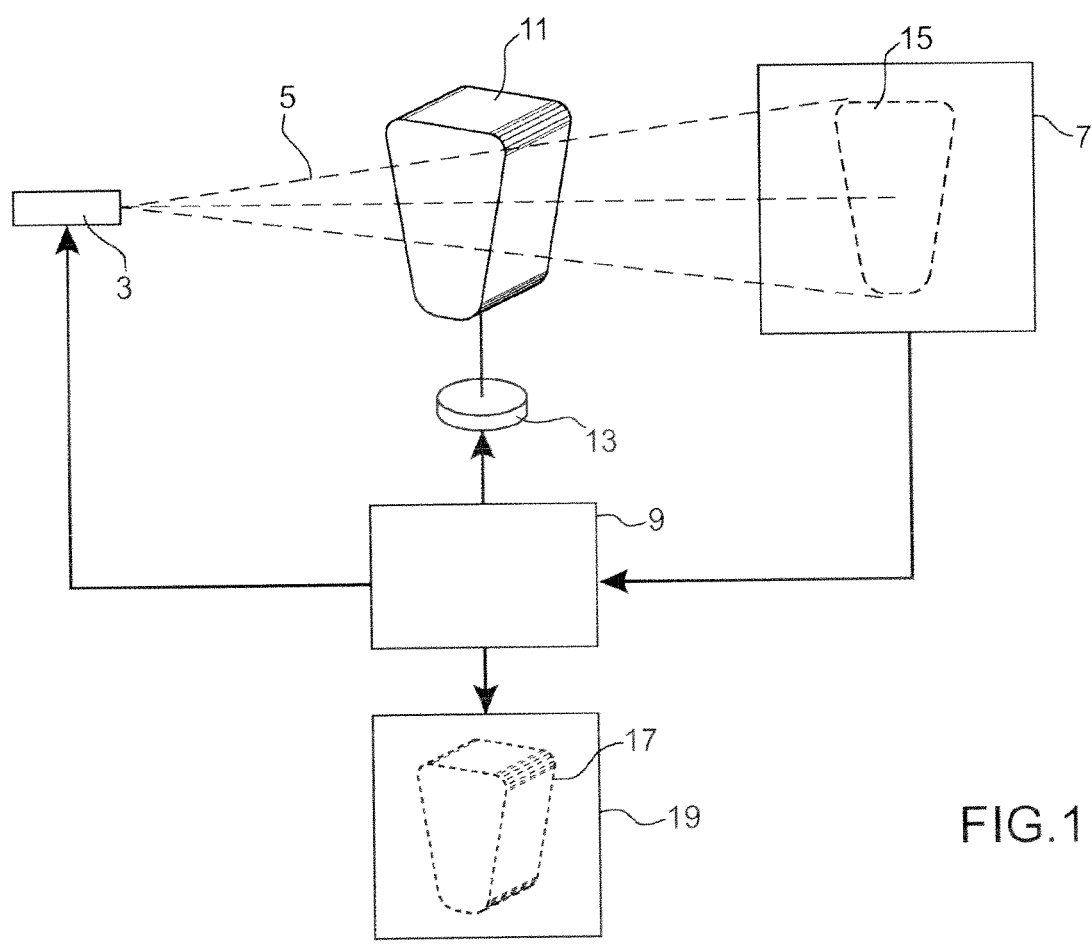
FIG. 1 illustrates schematically an example of a tomography system 1 that can be used for implementing the method according to the invention.

FIG. 1 illustrates highly schematically an example of a tomography system 1 that can be used for implementing the invention.

It should be noted that other tomography systems (such as helical tomography) may also be used for implementing the present invention.

The tomography system in FIG. 1 is non-intrusive and comprises a source 3 for emitting light rays 5, a detector 7, and processing means 9 (for example a computer or an information processor) coupled to the detector 7.

According to this example, the emission source is intended to emit X rays onto a part 11 fixed to a rotating plate or support 13, in line with the emission source, thus subjecting the part to radiography. The source 3 emitting the X rays, the rotating support 13 and the detector 7 are controlled by the processing means 9. The X rays passing through the part 11 and interacting with it are captured by the detector 7 measuring the attenuation of this flow of X rays. Various firings of X rays are carried out in various positions of the rotating support 13, enabling the detector 7 to form a series of radiographic images 15 corresponding to a series of projections of the part 11.

The series of projections enables the processing means 9 to reconstitute a volume (or tomographic) image 17 of the part 11 displayed on a screen 19. This is because the processing means 9 comprise a tomographic reconstruction algorithm intended to effect a reconstitution of a volume image 17. The tomographic reconstruction algorithm may be of the analytical or algebraic type using for example probabilistic criteria such as the maximum likelihood.

The reconstituted volume image 17 is formed by a three-dimensional grid of voxels, the values of which are proportional to the density of material. It should be noted that a voxel is a three-dimensional pixel representing the smallest volume unit. Thus the values of the voxels may indicate the disposition of any specific phase in corresponding zones of the part.

Figure 2:
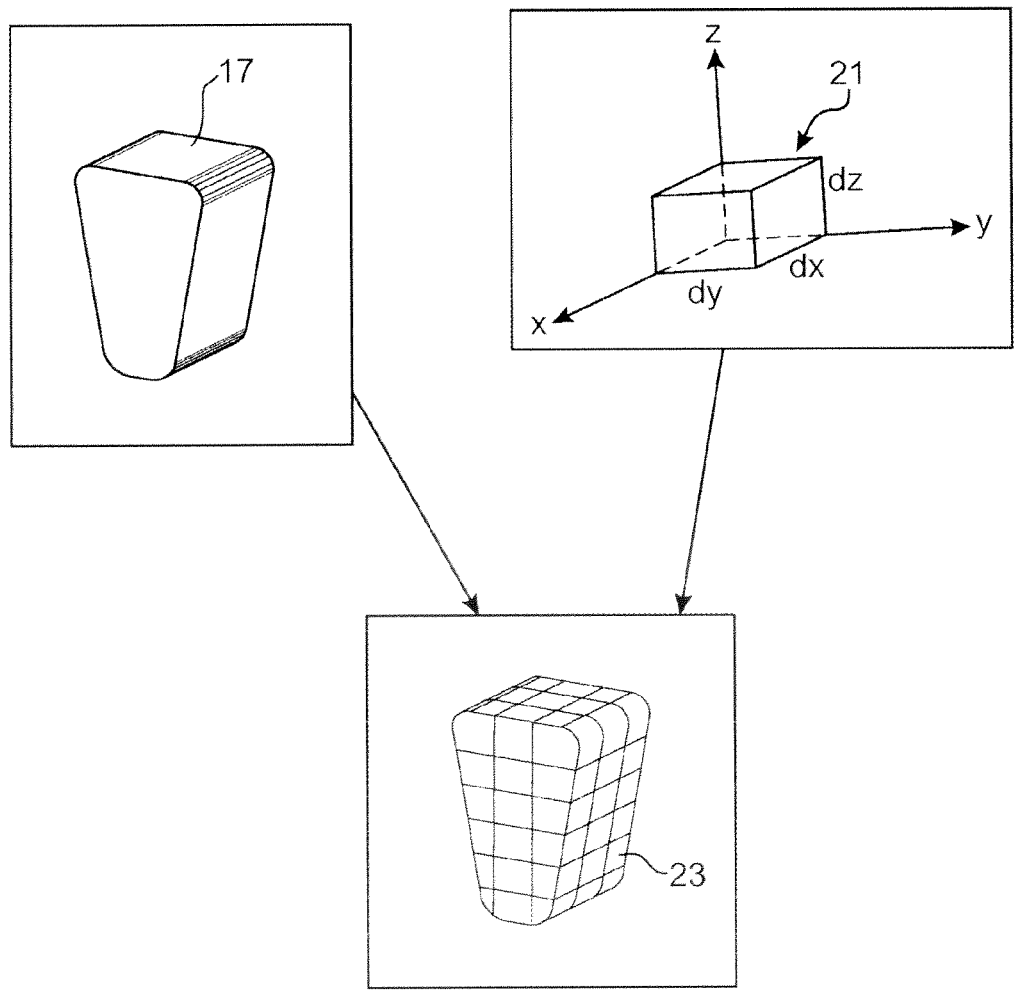
FIG. 2 is a functional diagram illustrating schematically a method for measuring the volume density of a specific phase in a part, according to the invention.

FIG. 2 is a functional diagram illustrating schematically a method for measuring the volume density of a specific phase in a part, according to the invention.

The inputs of this method comprise a volume image 17 and a predetermined reference volume 21. The latter is parallelepipedal in shape and is intended to be used as a reference for defining the density of the specific phase.

The output of this method comprises a volume density map 23 of the same size as the input volume image. In other words, the voxels of the volume image form a bijective relationship with the points on the map 23.

Thus, in accordance with the invention, the processing means 9 are configured to characterise the specific phase in the part 11 being inspected by defining, at each point on the map 23, the density of the specific phase with respect to the reference volume 21 whilst being free from the size of the latter.

More particularly, the processing means 9 are configured to associate a binary coefficient with each voxel of the volume image 17, thus constructing an initial three-dimensional matrix representation of binary coefficients. These binary coefficients represent the presence or absence of the specific phase being inspected in the zones of the part corresponding to the voxels.

Furthermore, the processing means 9 are configured to convolute the initial matrix representation with a convolution matrix kernel corresponding to the predetermined reference volume 21. Thus, for each coefficient of the matrix, it is possible to calculate the sum of the values of adjacent coefficients weighted by the convolution kernel. The convolution is carried out by effecting a composition of three successive monodimensional convolutions in three independent directions x, y, z, thus forming a resultant matrix representation, each resultant coefficient of which represents the volume ratio (density) of the specific phase in the reference volume 21. The decomposition of the convolution in three independent directions makes it possible to minimise the redundancy and to be free from the size of the reference volume 21 and even to be independent of the content of the volume image 17. Thus the number of computing steps according to the present invention is in O(N) and therefore very much reduced compared with the prior art, the algorithmic complexity of which is in O(NL), N being the number of voxels of the volume image and L the number of voxels of the reference volume.

The processing means 9 comprise a computer program comprising code instructions suitable for implementing the identification method according to the invention. It should be noted that the processing means 9 for reconstructing the volume image and the processing means for identifying the specific phase may correspond, according to a first variant, to the same processing unit and, according to a second variant, to two separate units.

Figure 3:
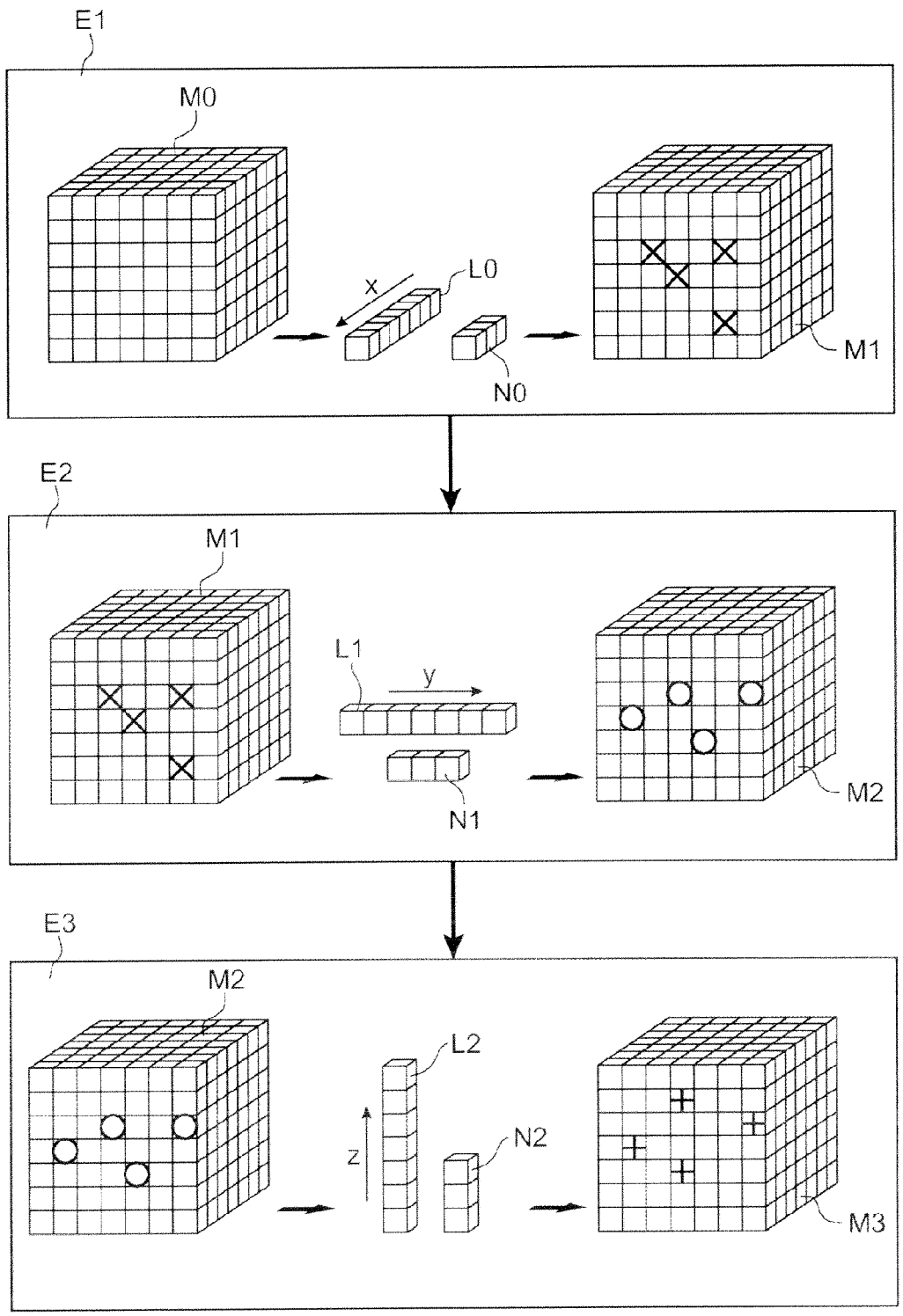
FIG. 3 illustrates schematically the convolution steps according to a preferred embodiment of the invention.

FIG. 3 illustrates schematically the convolution steps according to a preferred embodiment of the invention.

In step E1, the processing means are configured so as to extract each row of the initial matrix representation in a first direction (for example the x axis). Thus, for each row L0, a unidimensional signal is obtained that will be convoluted with the convolution kernel N0 in this first direction. The results of the convolution on all the lines thus form a first intermediate matrix representation M1. Advantageously, during the convolution, the support of the signal on each row is not modified.

Furthermore, the convolution of a row with an averaging kernel is calculated in one go, which is independent of the size of the kernel, by virtue of the fact that the voxel entering the kernel is added and the one emerging from the kernel is subtracted in order to have, at each position of the kernel, the sum of all the voxels covered by this kernel.

From the result obtained at the previous step, the same operation is performed in another independent direction. This is because, at step E2, the processing means are configured so as to extract each row L1 of the first intermediate matrix representation M1 in a second direction (for example the y axis) in order to convolute it with the convolution kernel N1 in this second direction, thus forming a second intermediate matrix representation M2.

Finally, at step E3, the processing means are configured so as to extract each row L2 of the second intermediate matrix representation M2 in the third direction not yet processed (the z axis) in order to convolute it with the convolution kernel N2 in this third direction, thus forming the resultant matrix representation M3.

Advantageously, the convolution kernel is an averaging kernel weighting each coefficient identically. The convolution kernel may thus correspond to a parallelepipedal reference volume of n×nm×p voxels with n, m, p integers for example from a few units to a few tens of units.

Furthermore, according to an advantageous aspect of the present invention, each current matrix representation (i.e. the first representation M1, the second representation M2 and the resultant representation M3) is constructed by replacing the coefficients of the previous matrix representation with current coefficients. In this case a buffer row is used to calculate the monodimensional convolution in each direction.

Moreover, the extraction and convolution operations on the various rows of each matrix representation M0, M1, M2 are advantageously parallelised. This is because the decomposition of the convolution in independent directions makes it possible carry out simultaneous computations on the various rows of each representation and consequently to fully exploit the power of the various computing units of the processing means 9. It should be noted that the synchronisation between the computing units is very discrete and non-blocking since it suffices to synchronise all these computing units, solely at the end of each step.

Figure 4:
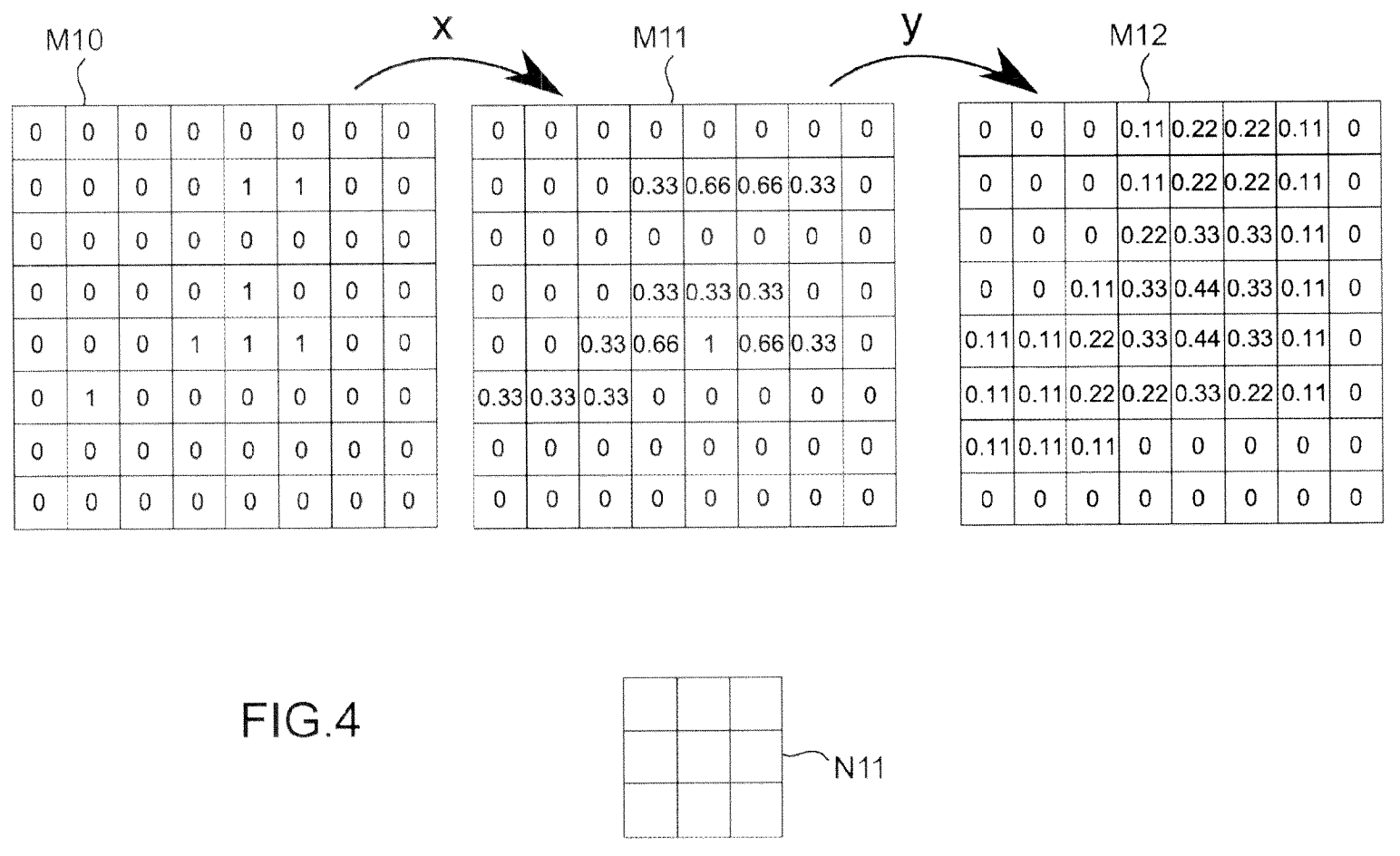

FIG. 4 is an example relating to a bidimensional image illustrating the convolution principle according to the invention.

For reasons of simplification, this example relates to a surface image, but the principle remains the same for a volume image.

At the start, an initial matrix M10 with binary coefficients $a_{ij}$ with i the number of the row and j the number of the column is associated with the image. The value "1" of a coefficient corresponds to the phase the volume density of which it is wished to measure and in contradistinction the value "0" corresponds to an absence of this phase.

The first step consists of extracting each row of the initial matrix along the x axis in order to convolute it with a convolution kernel corresponding to a predetermined reference surface along this axis. According to this example, the convolution kernel N11 is a 3×3 square matrix corresponding to a 9-pixel reference square. It is assumed that the convolution kernel N11 is an averaging kernel making it possible to take the average of each coefficient with its first neighbours. The results of the convolution on all the rows along the x axis form an intermediate matrix.

For example, on the second row of the initial matrix M10, the value of the coefficient $a_{24}$ is 0 ($a_{24}=0$) and the adjacent coefficients on the same row have the values 0 and 1 ($a_{23}=0$ and $a_{25}=1$). The average of the three coefficients $a_{23}$, $a_{24}$ and $a_{25}$, is then 0.33. Likewise, the average of the three coefficients $a_{24}$, $a_{25}$ and $a_{26}$ is 0.66. Thus, in order to form the intermediate matrix M11, the new current values are attributed to the coefficients of the matrix. For example, the initial values 0 and 1 of the coefficients $a_{24}$ and $a_{25}$ are replaced with the intermediate values 0.33 and 0.66 ($a_{24}=0.33$ and $a_{25}=0.66$).

From the intermediate matrix M11 obtained previously, the same operations along the y axis (i.e. along the columns of the matrix) are performed with the same convolution kernel N11. For example, on the fourth column of the intermediate matrix, the value of the coefficient $a_{24}$ is 0.33 (($a_{24}=0.33$) and the adjacent coefficients on the same column have the values 0 and 0 ($a_{14}=0$ and $a_{34}=0$). The average of the three coefficients $a_{14}$, $a_{24}$ and $a_{34}$ is then 0.11. In the resultant matrix M12, the intermediate value 0.33 of the coefficient $a_{24}$ is for example replaced with the resultant value 0.11 ($a_{24}=0.11$). The values of the coefficients of the resultant matrix M12 then correspond to the densities of the phase that it is wished to characterise.

The method of the present invention makes it possible to reduce the time taken for computing the volume ratio of a phase in a solid medium by several orders of magnitude (up to 4 orders of magnitude) compared with the prior art.

This is because, for a volume image of size 827×2024×1800 voxels and a reference volume of 41×41×41 voxels, the computing time according to the method of the present invention is only 40 seconds while the method offered by commercial software required a computing time of 5 hours 20 minutes (19,200 seconds). Thus the computing time was reduced by a factor of 450 compared with the prior art.

The method of the present invention can advantageously be used for production inspections in the aeronautical field and in particular for measuring the volume density of a specific phase in a part of an aircraft engine.

What is claimed is:

1. Method for the non-intrusive measurement of the volume density of a specific phase in a part, comprising the following steps:
   producing a volume image of said part, said image being formed by a three-dimensional grid of voxels, the values of which indicate the disposition of said specific phase in said part,
   associating a binary coefficient with each voxel of said volume image, thus constructing an initial three-dimensional matrix representation of binary coefficients, said binary coefficients representing a presence or absence of said specific phase in zones of said part corresponding to the voxels,
   convoluting said initial matrix representation with a convolution matrix kernel corresponding to a predetermined reference volume, said convolution being performed by effecting a composition of three monodimensional convolutions in three independent directions, thus forming a resultant matrix representation, each resultant coefficient of which represents a volume ratio of said specific phase in said reference volume,
   wherein said part is a part of an aircraft engine.

2. Method according to claim 1, wherein the convolution of said initial matrix representation comprises the following steps:
   extracting each row of said initial matrix representation in a first direction in order to convolute it with said convolution kernel in said first direction, thus forming a first intermediate matrix representation,
   extracting each row of said first intermediate matrix representation in a second direction in order to convolute it with said convolution kernel in said second direction, thus forming a second intermediate matrix representation, and
   extracting each row of said second intermediate matrix representation in a third direction in order to convolute it with said convolution kernel in said third direction, thus forming said resultant matrix representation.

3. Method according to claim 2, further comprising a parallelisation of the extraction and convolution operations on the various rows of each matrix representation.

4. Method according to claim 3, wherein each current matrix representation among the intermediate and resultant representations is constructed by replacing the coefficients of the previous matrix representation by current coefficients.

5. Method according to claim 1, wherein the convolution kernel is an averaging kernel weighting each coefficient identically.

6. Method according to claim 1, wherein the convolution kernel corresponds to a parallelepipedal reference volume.

7. System for non-intrusive measurement of the volume density of a specific phase in a part, comprising:
   processing means for producing a volume image of said part, said image being formed by a three-dimensional grid of voxels, the values of which indicate the disposition of said specific phase in said part,
   processing means for associating a binary coefficient with each voxel of said volume image, thus constructing an initial three-dimensional matrix representation of binary coefficients, said binary coefficients representing a presence or absence of said specific phase in zones of said part corresponding to the voxels,
   processing means for convoluting said initial matrix representation with a convolution matrix kernel corresponding to a predetermined reference volume, said convolution being performed by effecting a composition of three monodimensional convolutions in three independent directions, thus forming a resultant matrix representation, each resultant coefficient of which represents a volume ratio of said specific phase in said reference volume,
   wherein said part is a part of an aircraft engine.

8. System according to claim 7, further comprising:
   processing means for extracting each row of said initial matrix representation in a first direction in order to convolute it with said convolution kernel in said first direction, thus forming a first intermediate matrix representation,
   processing means for extracting each row of said first intermediate matrix representation in a second direction in order to convolute it with said convolution kernel in said second direction, thus forming a second intermediate matrix representation, and
   processing means for extracting each row of said second intermediate matrix representation in a third direction in order to convolute it with said convolution kernel in said third direction, thus forming said resultant matrix representation.

9. System according to claim 8, wherein the processing means are configured so as to parallelise extraction and convolution operations on the various rows of each matrix representation.

* * * * *